(12) United States Patent
Esser et al.

(10) Patent No.: US 8,455,447 B2
(45) Date of Patent: Jun. 4, 2013

(54) MODIFIED THERAPEUTIC AGENTS

(75) Inventors: Dirk Esser, Cologne (DE); Jason Richard Betley, Buntingford (GB); Simon Hugh Ridley, Cambridge (GB)

(73) Assignee: Adprotech Limited (GB)

( * ) Notice: Subject to any disclaimer, the term of this patent is extended or adjusted under 35 U.S.C. 154(b) by 234 days.

(21) Appl. No.: 12/688,252

(22) Filed: Jan. 15, 2010

(65) Prior Publication Data

US 2011/0086808 A1 Apr. 14, 2011

Related U.S. Application Data

(63) Continuation of application No. 10/526,808, filed as application No. PCT/GB03/03867 on Sep. 5, 2003, now abandoned.

(30) Foreign Application Priority Data

Sep. 5, 2002 (GB) .................................. 0220936.9

(51) Int. Cl.
| | | |
|---|---|---|
| *A61K 38/10* | (2006.01) | |
| *A61K 38/16* | (2006.01) | |
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |

(52) U.S. Cl.
USPC .......... 514/21.4; 530/326; 530/327; 530/328; 530/329; 530/330

(58) Field of Classification Search
None
See application file for complete search history.

(56) References Cited

U.S. PATENT DOCUMENTS

| 5,169,933 A | 12/1992 | Anderson et al. |
|---|---|---|
| 6,005,004 A | 12/1999 | Katz et al. |
| 6,713,606 B1 | 3/2004 | Smith et al. |
| 2003/0064431 A1 | 4/2003 | Mossakowska et al. |
| 2006/0241048 A1 | 10/2006 | Esser et al. |

FOREIGN PATENT DOCUMENTS

| WO | WO93/22343 | | 11/1993 |
|---|---|---|---|
| WO | WO98/02454 | | 1/1998 |
| WO | WO 98/39433 | * | 9/1998 |
| WO | WO00/16807 | | 3/2000 |
| WO | WO02/36612 | | 5/2002 |

OTHER PUBLICATIONS

Bader et al., Nature 407: 223-226 (2000).
Epand, Biopolymers 43(1): 15-24 (1997).
Schroeder et al., The Journal of Cell Biology 134(3): 647-660 (1996).
Hill, Anita; Protection of erythrocytes from human complement-mediated lysis by membrane-targeted recombinant soluble CD59: a new approach to PNH therapy; Blood; Mar. 1, 2006; vol. 107, No. 5; The Americian Society of Hematology.

* cited by examiner

*Primary Examiner* — Marcela M Cordero Garcia
(74) *Attorney, Agent, or Firm* — Perkins Coie LLP

(57) ABSTRACT

The invention provides a modified therapeutic agent, said modified agent comprising three or more membrane binding elements with low membrane affinity covalently associated with the agent which elements are capable of interacting independently and with thermodynamic additivity, with components of cellular or artificial membranes exposed to extracellular fluids wherein at least two membrane binding elements are lipophilic elements, which may be aliphatic acyl groups, which may be selected from the list consisting of Myristoyl, Decanoyl or Hexanoyl.

28 Claims, 1 Drawing Sheet

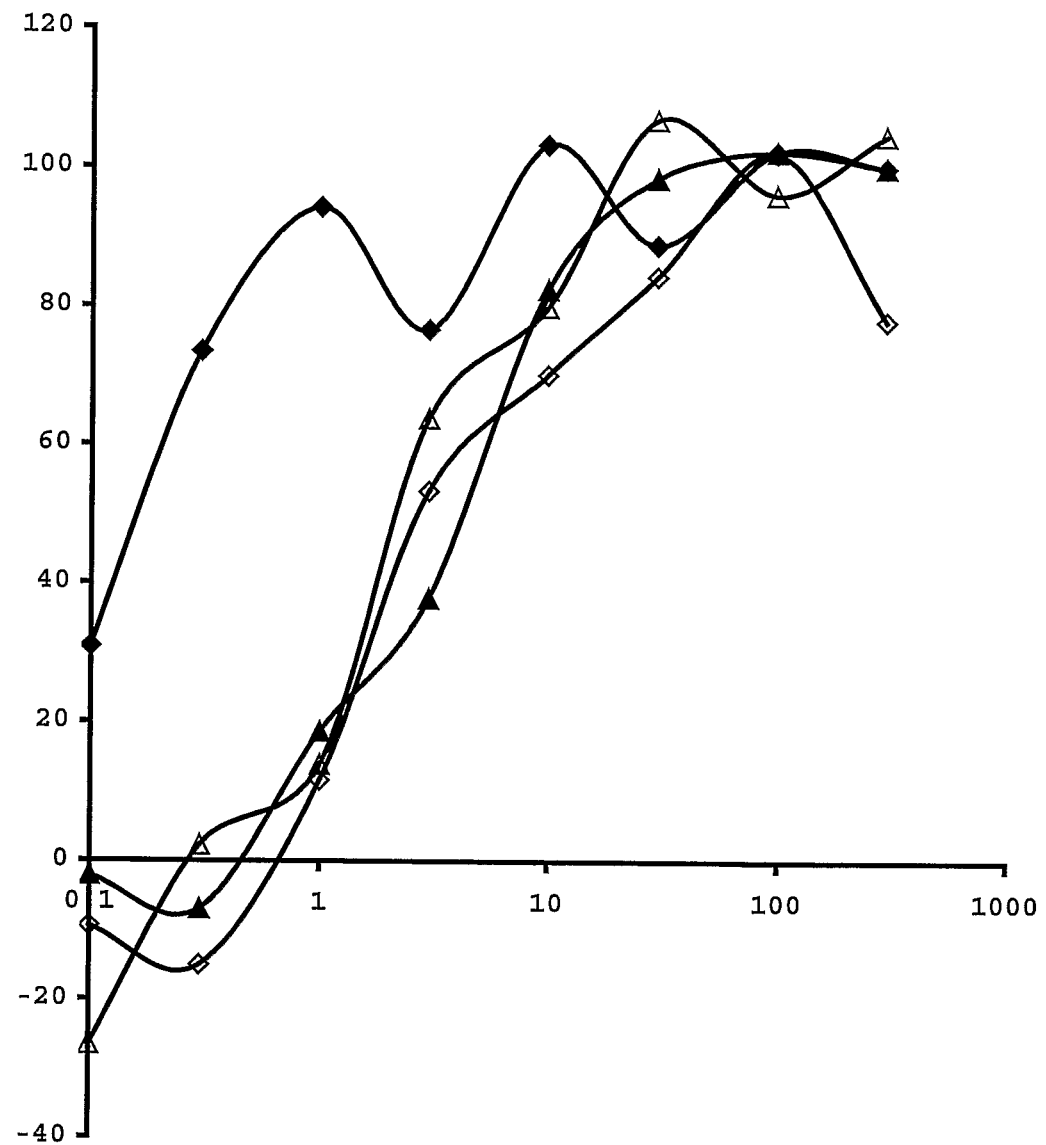

MODIFIED THERAPEUTIC AGENTS

This application is a continuation of U.S. application Ser. No. 10/526,808 filed Jun. 8, 2005, which is a 371 of PCT/GB03/003867, filed Sep. 5, 2003. The entire contents of the above-identified application are hereby incorporated by reference.

This invention relates to modified therapeutic agents, their use in therapy and intermediates. More particularly it relates to soluble therapeutic agents containing membrane binding elements.

Many drugs are administered in a pharmaceutical solution with the drug dissolved in a physiological solution suitable for injection. Further, other drugs are administered in a dry form such as a tablet. In this form, the tablet dissolves after administration releasing the drug, which is absorbed into the bloodstream where it will be transported, by the blood, to its site of action. Whatever form the drug is administered in it is transported in soluble form within the bloodstream.

Biotechnology has increased the number of potential drugs that are proteins or protein based. Essentially all protein drugs are administered as solutions and function in vivo in the solution phase. In biochemistry and pharmacology, however, a large number of control and mediator proteins are associated with or function within or on the plasma membranes of cells. Except for soluble, truncated versions of one class of these molecules, no membrane-associated proteins have been developed as therapeutic agents. There are two main reasons for this situation. Firstly, overexpression of proteins that are retained in the membranes of the producer cells is limited by the low capacity of membranes for proteins and often by the toxic effects of retention when expression is intrinsically efficient. Secondly, extraction of these proteins from membranes requires detergents or organic solvents, often results in inactivation of the protein, leads to difficulties in achieving the high purity needed for drug use and usually gives a product which is hard to formulate for intravenous administration.

Soluble, truncated versions of membrane-associated proteins overcome the production difficulties associated with full length proteins. However such truncated molecules lack the membrane binding capability and specificity of the full length proteins which properties may be advantageous or even essential to the desired therapeutic activity. In addition, the biological action of other chemically derived drugs may benefit from being targeted to or within close proximity to, a cellular membrane.

WO 98/02454 describes a soluble derivative of a soluble polypeptide which comprises two or more heterologous membrane binding elements with low membrane affinity covalently associated with the polypeptide which elements are capable of interacting, independently and with thermodynamic additivity (Dill, K. A. J. Biol. Chem. 1997. 272, 701-704), with components of cellular or artificial membranes exposed to extracellular fluids ie. to the external surface of the cell or artificial membrane.

By 'heterologous' is meant that the elements are not found in the native full length protein from which a soluble protein may be derived.

By 'soluble polypeptide' is meant a truncated derivative of a full length protein which lacks its natural membrane binding capability, and/or a polypeptide which has a solubility level in aqueous media of >100 µg/ml.

By 'membrane binding element with low membrane affinity' is meant that the element has a measurable but relatively low affinity for membranes, that is a dissociation constant greater than 1 µM, preferably 1 µM-1 mM. The elements preferably have a size <5 kDa.

A modified therapeutic agent has sufficient membrane binding elements with low affinities for membrane components to result in a derivative with a high (preferably 0.01-10 nM dissociation constant) affinity for specific membranes. The elements combine so as to create an overall high affinity for the particular target membrane but the combination lacks such high affinity for other proteins for which single elements may be (low-affinity) ligands.

The elements should be chosen so as to retain useful solubility in pharmaceutical formulation media, preferably >100 μg/ml.

Surprisingly, we have now found that an intermediate in the preparation of a modified therapeutic agent, namely three linked membrane binding elements, consisting of a basic amino acid element and two lipophilic elements remains soluble when prepared and isolated.

When modifying a therapeutic agent, the membrane binding elements can be added sequentially, with the first conjugated to the therapeutic agent, then subsequent elements being conjugated to each other. A second method of modifying the agent is to prepare the membrane binding elements separately, conjugate the elements to each other first, isolate the whole and then conjugate the preparation to the therapeutic agent.

When modifying peptides and proteins, the membrane binding element preparation (known as a “tail”) is preferably soluble in aqueous solutions. This is to avoid the use of solvents to dissolve the tail prior to the conjugation to the peptide, which may damage the peptide. It is a surprising feature of the present invention that a tail with two lipophilic binding elements may be soluble in aqueous solution.

Further, when this soluble tail was added to a therapeutic agent the resultant modified therapeutic agent remained soluble.

In addition, it was found that a modified therapeutic agent containing this highly lipophilic tail had a lower affinity for serum albumin as compared to a therapeutic agent with only a single lipophilic membrane binding element. Under certain circumstances this reduced serum albumin affinity is preferable, potentially increasing the binding of the agent to cellular membranes.

The present invention therefore provides a modified therapeutic agent, said agent comprising three or more membrane binding elements wherein at least two elements are lipophilic.

The two lipophilic membrane binding elements may be different but preferably will be identical.

The lipophilic membrane binding elements are preferably a $C_{6-20}$ fatty acyl derivative of an amino $C_{2-6}$ alkane thiol (optionally C-substituted) such as N-(2-myristoyl)aminoethanethiol or N-myristoyl L-cysteine.

However, other elements will be known to those in the art. In general the lipophilic membrane binding element is defined as;

having from 6 to 30, carbon atoms including those of any aromatic rings, if present;

being straight or branched (for example having two or three branch points);

saturated or unsaturated (for example containing one or more double or triple bonds);

having one or more (such as 1, 2, 3 or 4) heteroatoms independently selected from S, O, or N;

optionally, containing one or more, for example two or three aromatic rings, which may or may not be fused and each of which may contain from one or more (such as 1, 2, 3 or 4) heteratoms which, if present, are independently selected from N, O, or S and;

optionally having one or more (such as 1, 2, or 3) substituents selected from hydroxy, —SH, amino and halo (where halo is fluoro, chloro, bromo or iodo).

Preferably, the aromatic rings are six-membered, and may be selected from benzene and pyridine. If the rings are fused, then they may be selected from naphthalene, anthracene, quinolene and isoquinolene. Other examples of aromatic rings include thiophene and pyrrole.

The therapeutic agent can be a therapeutic protein or peptide. A therapeutic protein is a protein that has a biological effect on a region in the body on which it acts or on a region of the body on which it remotely acts via intermediates. The invention thus promotes localisation of such a therapeutic protein at cellular membranes and thereby provides one or more of several biologically significant effects with potential therapeutic advantages.

In this specification to terms polypeptide, protein and peptide are synonymous and are used interchangeably. The term therapeutic protein is the term used to define a protein, polypeptide or peptide that has a therapeutic effect when administered to the body.

Most importantly, the modifying lipophilic tail promotes localisation of the therapeutic agent to cellular membranes without significant binding to blood serum albumin and thereby reduces the amount of protein lost to indirect serum binding and increases the amount that is available to bind to the desired cellular membrane.

A modified therapeutic agent as described may be used in association with artificial membranes or mimics thereof to allow delivery of the therapeutic agent to sites where it will provide therapeutic benefit.

Examples of therapeutic proteins that may be modified according to the invention include but are not limited to the following:

TABLE 1

Therapeutic Proteins

| Base Protein | Cell Target | Therapeutic Application |
|---|---|---|
| IL-4 Y124D mutein | B-cells | Anti-allergy (IL-4 antagonist) |
| Plasminogen activators e.g. Prourokinase, streptokinase, tissue-type plasminogen activator, reteplase | Erythrocytes, vascular endothelium | Prevention of venous thrombosis |
| Leptin | Choroid plexus, Hypothalamus | Weight loss (agonist) |
| Complement inhibitors* | Vascular endothelium, Myocytes, Erythrocytes, Lymphocytes | Ischaemic injury, transplantation inflammation |
| scFv antibody against cytokines | Eosinophils | Asthma, Allergic disease |
| Protein C | Vascular endothelium | Prevention of venous thrombosis |
| Antibodies against CD4, B7/CD28, CD3/TCR, CD11b (CR3) | Lymphocytes | Immunosuppression |
| Interferon-β and derivatives | Lymphocytes | Immunomodulation, Multiple sclerosis |

*CR1 (CD35); DAF (CD55); MCP (CD46); CD59; Factor H C4 binding protein; and hybrids or muteins thereof such as CR1-CD59 chimeras.

Examples of non-protein therapeutic agents include but are not limited to anti-infectives such as antibacterial, antimicrobial, and antifungal agents such as amphotericin; cytotoxic agents such as paclitaxel and doxorubicin; corticosteroids agents such as dexamethasone; other cell surface acting therapeutic agents will be well known to those in the art.

Importantly the invention comprises two (or more) lipophilic membrane binding elements. However, additional membrane binding elements are preferably selected from: basic amino acid sequences; ligands of known integral membrane proteins; sequences derived from the complementarity-determining region of monoclonal antibodies raised against epitopes of membrane proteins; membrane binding sequences identified through screening of random chemical or phage display libraries.

Suitable examples of amino acid sequences comprising basic amino acids include:

| i)    | DGPKKKKKKSPSKSSGC   | [SEQ ID NO: 1] |
| ii)   | GSSKSPSKKKKKKPGDC   | [SEQ ID NO: 2] |
| iii)  | SPSNETPKKKKKRFSFKKSG | [SEQ ID NO: 3] |
| iv)   | CDGPKKKKKKSPSKSSK   | [SEQ ID NO: 4] |
| v)    | SKDGKKKKKKSKTKC     | [SEQ ID NO: 5] |
| vi)   | GSSKSPSKKDDKKGDC    | [SEQ ID NO: 6] |
| vii)  | GSSKSPSKDKDKDGDC    | [SEQ ID NO: 7] |
| viii) | KSSKSPSKKDDKKPGDC   | [SEQ ID NO: 8] |
| ix)   | KSSKSPSKDKDKDPGDC   | [SEQ ID NO: 9] |

(N-terminus on left)

In addition, it would be envisaged that smaller basic elements could be used that still retain the necessary properties of the invention, for example KSKKKC [SEQ ID NO: 10]. These would have a number of advantages including the cost of production of modified therapeutic agent incorporating such peptide sequence.

Examples of amino acid sequences derived from ligands of known integral membrane proteins include RGD-containing peptides such as GRGDSP [SEQ ID NO: 11] which are ligands for the $\alpha_{IIb}\beta_3$ integrin of human platelet membranes. Another example is DGPSEILRGDFSSC [SEQ ID NO: 12] derived from human fibrinogen alpha chain, which binds to the GpIIb/IIIa membrane protein in platelets.

Further examples of such sequences include those known to be involved in interactions between membrane proteins such as receptors and the major histocompatibility complex. An example of such a membrane protein ligand is the sequence GNEQSFRVDLRTLLRYA [SEQ ID NO: 13] which has been shown to bind to the major histocompatibility complex class 1 protein (MHC-1) with moderate affinity.

Yet further examples of such sequences employ a membrane insertive address specific for T-cells. Such a sequence is derived from the known interaction of the transmembrane helix of the T-cell antigen receptor with CD3. Examples are peptides containing the sequence GFRILLKV [SEQ ID NO: 14].

An example of a ligand for an integral membrane protein is the carbohydrate ligand Sialyl Lewis$^x$ which has been identified as a ligand for the integral membrane protein ELAM-1.

Sequences derived from the complementarity-determining regions of monoclonal antibodies raised against epitopes within membrane proteins are also suitable membrane binding elements, as are binding sequences from random chemical libraries such as those generated in a phage display format and selected by biopanning operations in vitro.

Optionally, conditional dissociation from the membrane may be incorporated into agents of the invention using mechanisms such as pH sensitivity, regulation through metal ion binding (using endogenous $Ca^{2+}$, $Zn^{2+}$ and incorporation of ion binding sites in membrane binding elements) and protease cleavage (e.g plasminolysis of lysine-rich membrane binding sequences to release and activate prourokinase).

Peptidic membrane binding elements are preferably located sequentially either at the N or C terminus of the agent. The amino acid sequences are linked to one another and to the soluble agent by linker groups which are preferably selected from hydrophilic and/or flexible amino acid sequences of 4 to 20 amino acids; linear hydrophilic synthetic polymers; and chemical bridging groups. They can also be linked directly via a suitable bond such as the native amide bond.

Peptides and peptide linkages may be made chemically or biosynthetically by expression of appropriate coding DNA sequences. Non peptide linkages may be made chemically or enzymatically by post-translational modification.

Chemical bridging groups and reagents suitable for their formation are known to those skilled in the art. For example, where the polypeptide portion of the agent of the invention and a peptidic membrane binding element both include a single cysteine the linkage between the two will take the form —S—S—. This is generated by conventional disulphide exchange chemistry, by activating a thiol on one polypeptide and reacting the activated thiol with a free thiol on the other polypeptide. Such activation procedures make use of disulphides which form stable thiolate anions upon cleavage of the S—S linkage and include reagents such as 2,2' dithiopyridine and 5,5'-dithio(2-nitrobenzoic acid, DTNB) which form intermediate mixed disulphides capable of further reaction with thiols to give stable disulphide linkages.

Also, a free thiol function can be introduced by reaction of a polypeptide with 2-iminothiolane, N-succinimidyl 3-(2-pyridyldithio) propionate (with subsequent reduction) or N-acetyl homocysteine thiolactone. This will permit coupling of the protein attachment group with a thiol-reactive group. Alternatively, the protein attachment group can contain a thiol-reactive entity such as the 6-maleimidohexyl group or a 2-pyridyl-dithio group which can react with a free thiol. Preferably, the protein attachment group is derived from protein modifying agents such as 2-iminothiolane that react with lysine s-amino groups in proteins.

After the linkage reaction, the conjugate can be isolated by a number of chromatographic procedures such as gel filtration, ion-exchange chromatography, affinity chromatography or hydrophobic interaction chromatography. These procedures may be either low pressure or high performance variants.

The conjugate may be characterised by a number of techniques including low pressure or high performance gel filtration, SDS polyacrylamide gel electrophoresis or isoelectric focussing.

The agents of this invention are preferably administered as pharmaceutical compositions.

Accordingly, the present invention also provides a pharmaceutical composition comprising an agent of the invention and a pharmaceutically acceptable excipient.

The quantity of material administered will depend upon the potency of the agent and the nature of the complaint be decided according to the circumstances by the physician supervising treatment. However, in general, an effective amount of the polypeptide for the treatment of a disease or disorder is in the dose range of 0.01-100 mg/kg per day, preferably 0.1 mg-10 mg/kg per day, administered in up to five doses or by infusion.

The invention also provides an agent of the invention for use as a medicament.

The invention further provides a method of treatment of disorders amenable to treatment by a therapeutic agent which comprises administering a modified therapeutic agent according to the invention, and the use of an agent of the invention for the preparation of a medicament for treatment of such disorders.

DRAWINGS

FIG. 1. A graph of percentage inhibition of haemolysis in the presence (empty symbol) or absence (filled symbol) of Serum albumin. -◇- APT070 (single myristoyl group), and -Δ- APT3098 (two lipophilic (myristoyl) elements).

Note: APT070 is the composition [SCR1-3]-Cys-S—S-[MSWP-1] SEQ ID NO: 8 of Example 8 of WO98/02454.

EXAMPLES

Synthesised Bis Acylated Membrane Binding Tails

The following compounds were synthesised each containing two fatty acid membrane binding elements and a basic element. The fatty acid membrane binding element consisted of either a Myristoyl, Hexanoyl or Decanoyl group.

TABLE 2

Binding Membrane Element Reference No.

| Peptide | Sequence | SEQ ID No. |
|---------|----------|------------|
| APT3098 | bis-myristoyl-KSSKSPSKKDDKKPGDC | 15 |
| APT3328 | bis-myristoyl-KSSKSPSKDKDKDPGDC | 16 |
| APT3329 | bis-myristoyl-KSKKKC | 17 |
| APT3330 | bis-Decanoyl-KSSKSPSKKDDKKPGDC | 18 |
| APT3331 | bis-Decanoyl-KSSKSPSKDKDKDPGDC | 19 |
| APT3332 | bis-Decanoyl-KSKKKC | 20 |
| APT3333 | bis-Hexanoyl-KSSKSPSKKDDKKPGDC | 21 |
| APT3334 | bis-Hexanoyl-KSSKSPSKDKDKDPGDC | 22 |
| APT3335 | bis-Hexanoyl-KSKKKC | 23 |

The bis acylated (underivatised) peptides were activated via thiopyridylation by reaction with Aldrithiol-2.

Aldrithiol-2 (110.2 mg, 500 µmol) was dissolved in acetonitrile (2 mL) to yield a 250 mM solution. Each of the underivatised peptides (see below for amounts) was dissolved in water (1 mL) and 3 equivalents of Aldrithiol-2 (in solution) were added.

The reaction mixtures were stirred for 2 h.

Purification of APT3328, APT3333, APT3334, APT3335

The target molecule was isolated by preparative HPLC and the majority of the solvent was removed under reduced pressure to leave ~2 mL of aqueous solution. This solution was lyophilised to yield a fluffy white solid.

Purification of APT3329

The target molecule was isolated by preparative HPLC and the majority of the solvent was removed under reduced pressure, causing a white solid to precipitate out of solution.

DMSO (2 mL) was added to dissolve the precipitate and the remaining water removed under reduced pressure.

Purification of APT3330, APT3331 and APT3332

The target molecule co-eluted with excess Aldrithiol-2 upon preparative HPLC. The majority of the solvent was removed under reduced pressure to leave ~2 mL of aqueous solution, which was transferred to a lyophilisation vial (10 mL size). Ethyl acetate (2 mL) was added, the vial shaken and the aqueous/organic layers left to separate. The organic (top) layer was removed using a Pasteur pipette. This extraction process was repeated three times (3×2 mL ethyl acetate) and the target molecule isolated by preparative HPLC. The majority of the solvent was removed under reduced pressure to leave ~2 mL of aqueous solution. This solution was lyophilised to yield a fluffy white solid.

Conjugation of Membrane Binding Peptide to SCR1-3 (APT154)

The bis acylated membrane binding peptides were conjugated to SCR1-3 (APT154) using activated peptides.

APT154 solution (100 µM, 5 mL, 0.5 µmol) in sodium phosphate buffer (0.1 M, pH 6.0) was reduced with TCEP (1.5 µmol, 150 µL of a 10 mM stock, 3 equivalents) by leaving overnight at room temperature.

APT154 (60 nmol, 600 µL of the reduced stock solution, allowing for a final concentration of 40 µM in 1.5 mL) was added to each of activated peptide (10 equivalents, 600 nmol in DMSO). Citrate buffer (pH 6.0, 808.4 µL) was added to the eight reaction mixtures to make the volume up to 1.5 mL in each.

The mixtures were left for 2 h at RT. Conjugation was assessed by SDS-PAGE.

The SDS-PAGE showed that APT3329, 3332, and 3335 had not successfully conjugated.

Anti-Haemolytic Assays

The Anti-complement activity of the modified SCR1-3 agents was measured by classical pathway mediated haemolysis of sheep erythrocytes.

Anti-Complement Activity of Acylated Peptide/APT154 Conjugates

Step 1—The Dilution Plate 7 wells of each of 9 lanes, missing the uppermost well, on a flat-bottomed microtitre plate were filled with 200 µL of diluent (0.100 M Hepes, 0.150 M NaCl, 0.100% gelatin, adding NaOH to pH 7.4).

Into the uppermost wells, the required volume of each test/control sample was aliquotted, immediately followed by enough diluent to make the total volume up to 300 µL, to ensure a final concentration of 1.2 µM.

Using a multichannel Gilson pipette, all 9 top wells were mixed and 100 µL were transferred from these wells to the corresponding wells in $2^{nd}$ row.

Using the multichannel Gilson pipette, and after mixing thoroughly, a further 22 µL was transferred from the $2^{nd}$ row into the $4^{th}$, 22 µL from the $4^{th}$ row to the $6^{th}$ and a further 22 µL was transferred form the $6^{th}$ row to the $8^{th}$.

Similarly 22 µL from wells in the top row were transferred to the $3^{rd}$, 22 µL from those in the $3^{th}$ row to the $5^{th}$ and finally 22 µL from the $5^{th}$ row were transferred to the $7^{th}$, creating a 3 log dilution gradient. At each step it was made sure that the wells were mixed thoroughly.

Step 2—The Reaction Plate

Using a multichannel Gilson 100 µL of diluent were pipetted into all wells of column A on two V-bottomed microtitre plate and 50 µL of diluent into all wells of column B. These lanes formed the background ($A_o$) and 100% ($A_{max}$) controls. 50 µL from each well of the APT154 dilution series (lane 1 of the dilution plate) were transferred into lanes 3 and 4 of the first reaction plate. Each sample was tested in duplicate on the reaction plate. This procedure was repeated for the remaining samples.

15.8 mL of diluent and 160 µL of pig serum was mixed by swirling in a polypropylene universal tube. This diluted serum was tipped into a square petri dish (100×100 mm). 50 µL of this solution was transferred to each well of the two reaction plates, except for the wells of each column A, using the multichannel Gilson pipette.

8 tubes (4 for each reaction plate) of sensitised sheep red blood cells were shaken rapidly for a few seconds to resuspend the cell pellet until the solution was a uniform pink colour. These were emptied into a new 100×100 mm petri dish and were mixed by swirling the tray gently. Using the multichannel Gilson, 100 µL of the RBC suspension was transferred into each well of the two reaction plates.

Precut pieces of Nescofilm were placed across the open wells of the two reaction plates and were incubated at 37° C. for 1 hour, without shaking.

Step 3: Processing of Plate

After incubation the plates were centrifuged at 1600 rpm for 3 min and the Nescofilm removed. 150 µL of supernatant from each well of the two plates was then transferred into the corresponding wells of two new microtitre plates and the absorbance of each well measured at 405 nm using a plate reader.

Calculation of % Inhibition

% inhibition was calculated using the following formula:

$$1 - \left(\frac{t - A_o}{A_{max} - A_o}\right) \times 100\%$$

wherein:

$A_o$=the mean value of the absorbances in lane 1

$A_{max}$=the mean value of the absorbances in lane 2 t=the mean of the two absorbance values for each sample at any given concentration.

Haemolytic Assay Data

The table below shows the percentage inhibition average data from both assays (i.e. four wells of the reaction plates) for each polypeptide.

Average absorbances at 405 nm $A_o$=0.033 $A_{max}$=0.204

TABLE 3

Percentage inhibition of haemolysis for modified therapeutic agents

| | Compound | | | | | |
|---|---|---|---|---|---|---|
| Conc/nM | APT154 | APT3328 | APT3330 | APT3331 | APT3333 | APT3334 |
| 300 | 112.66 | 106.74 | 110.44 | 105.85 | 107.48 | 110.29 |
| 100 | 97.11 | 106.14 | 103.48 | 108.96 | 101.41 | 98.59 |

TABLE 3-continued

Percentage inhibition of haemolysis for modified therapeutic agents

| | Compound | | | | | |
|---|---|---|---|---|---|---|
| Conc/nM | APT154 | APT3328 | APT3330 | APT3331 | APT3333 | APT3334 |
| 30 | 73.58 | 107.33 | 106.88 | 106.59 | 69.13 | 68.39 |
| 10 | 45.00 | 87.19 | 105.40 | 106.29 | 38.79 | 42.93 |
| 3 | 32.12 | 48.56 | 100.96 | 91.93 | 14.66 | 17.02 |
| 1 | 8.88 | 37.45 | 80.53 | 64.84 | 15.25 | 10.21 |
| 0.3 | 3.11 | 15.69 | 43.97 | 29.61 | 17.76 | 7.55 |
| 0.1 | 7.40 | 5.33 | 23.09 | 19.84 | 8.44 | 8.59 |

The assay showed that the addition of the various membrane binding elements did not greatly affect the activity of the SCR1-3 peptide.

Anti-Complement Activity of Acylated Peptide/APT154 Conjugates in the Presence of Bovine Serum Albumin (BSA)

Step 1—The Dilution Plate

BSA (320 mg) was dissolved in diluent (20 mL, 0.100 M Hepes, 0.150 M NaCl, 0.100% gelatin, adding NaOH to pH 7.4). 7 wells of each of 4 lanes, missing the uppermost well, on a flat-bottomed microtitre plate were filled with 200 µL of the BSA/diluent solution. Into the uppermost wells, the required volume each test/control sample (APT3328, APT33330, APT33331 and APT070) was aliquotted, immediately followed by enough BSA/diluent solution to make the total volume up to 300 µL, to ensure a final concentration of 1.2 µM.

These 1.2 µM wells were then diluted across a 3 log dilution gradient and the rest of the assay performed as for the peptide/APT154 conjugates. The BSA diluent solution was used instead of pure diluent except for the $A_o$ lane of the reaction plate, for which pure diluent (50 µL) and the BSA/diluent solution (50 µL) were aliquotted. The whole assay was repeated.

Haemolytic Assay Data

The two tables (Table 4 and 5) below show the average data from both assays (i.e. four wells of the reaction plates)

Average absorbances at 405 nm $A_o$=0.040 $A_{max}$=0.184

TABLE 4

Average absorbance data for modified therapeutic agents with BSA.

| | Compound | | | |
|---|---|---|---|---|
| Conc/nM | APT070 | APT3328 | APT3330 | APT3331 |
| 300 | 0.042 | 0.051 | 0.049 | 0.060 |
| 100 | 0.050 | 0.052 | 0.051 | 0.056 |
| 30 | 0.064 | 0.093 | 0.075 | 0.066 |
| 10 | 0.069 | 0.131 | 0.111 | 0.120 |
| 3 | 0.143 | 0.163 | 0.171 | 0.176 |
| 1 | 0.168 | 0.186 | 0.182 | 0.183 |
| 0.3 | 0.189 | 0.198 | 0.192 | 0.202 |
| 0.1 | 0.199 | 0.205 | 0.190 | 0.193 |

TABLE 5

Average % Inhibition for modified therapeutic agents with BSA

| | Compound | | | |
|---|---|---|---|---|
| Conc/nM | APT070 | APT3328 | APT3330 | APT3331 |
| 300 | 98.84 | 93.02 | 94.35 | 86.53 |
| 100 | 93.35 | 92.02 | 92.85 | 89.69 |
| 30 | 84.21 | 64.92 | 76.56 | 82.54 |
| 10 | 80.71 | 39.65 | 52.62 | 46.80 |
| 3 | 31.50 | 18.20 | 12.88 | 9.73 |
| 1 | 14.88 | 3.24 | 5.57 | 4.90 |
| 0.3 | 1.08 | −5.07 | −0.91 | −7.56 |
| 0.1 | −5.40 | −9.39 | 0.58 | −1.91 |

Anti-Complement Activity of Acylated Peptide/APT154 Conjugates in the Absence and Presence of BSA Absence of BSA Step 1—The Dilution Plate 7 wells of each of 5 lanes, missing the uppermost well, on a flat-bottomed microtitre plate were filled with 200 µL of diluent (0.100 M Hepes, 0.150 M NaCl, 0.100% gelatin, adding NaOH to pH 7.4).

Into the uppermost wells, the required volume of each test/control sample was aliquotted, immediately followed by enough diluent to make the total volume up to 300 µL, to ensure a final concentration of 1.2 µM.

The specific volumes of each sample used, along with the designated lanes for each are shown below.

These 1.2 µM wells were then diluted across a 3 log dilution gradient and the rest of the assay performed as for the peptide/APT154 conjugates.

Presence of BSA

The method used was as that above for the assay in the absence of BSA, using BSA/diluent solution (160 mg BSA in 10 mL diluent) instead of pure diluent. In the $A_o$ lane of the reaction plate, for which pure diluent (50 µL) and the BSA/diluent solution (50 µL) were aliquotted.

Haemolytic Assay Data

Average absorbances at 405 nm

No BSA $A_o$=0.025 $A_{max}$=0.213

With BSA $A_o$=0.057 $A_{max}$=0.190

TABLE 6

Average absorbance data for modified therapeutic agents without BSA.

| | Without BSA | | | | |
|---|---|---|---|---|---|
| Conc/nM | APT070 | APT3098 | APT3328 | APT3330 | APT33331 |
| 300 | 0.025 | 0.025 | 0.016 | 0.026 | 0.019 |
| 100 | 0.021 | 0.021 | 0.024 | 0.025 | 0.025 |

TABLE 6-continued

Average absorbance data for modified therapeutic agents without BSA.

| | Without BSA | | | | |
|---|---|---|---|---|---|
| Conc/nM | APT070 | APT3098 | APT3328 | APT3330 | APT33331 |
| 30 | 0.046 | 0.028 | 0.061 | 0.018 | 0.021 |
| 10 | 0.019 | 0.058 | 0.099 | 0.023 | 0.042 |
| 3 | 0.069 | 0.142 | 0.173 | 0.031 | 0.041 |
| 1 | 0.036 | 0.178 | 0.203 | 0.093 | 0.109 |
| 0.3 | 0.075 | 0.226 | 0.221 | 0.162 | 0.170 |
| 0.1 | 0.155 | 0.217 | 0.222 | 0.188 | 0.185 |

$A_o = 0.025$
$A_{max} = 0.213$

TABLE 7

Average % Inhibition data for modified therapeutic agents without BSA.

| | Without BSA | | | | |
|---|---|---|---|---|---|
| Conc/nM | APT070 | APT3098 | APT3328 | APT330 | APT3331 |
| 300 | 100.00 | 100.00 | 104.79 | 99.73 | 103.46 |
| 100 | 102.13 | 102.13 | 100.80 | 100.27 | 100.00 |
| 30 | 88.83 | 98.40 | 81.12 | 103.72 | 102.13 |
| 10 | 103.19 | 82.45 | 60.64 | 101.33 | 91.22 |
| 3 | 76.60 | 37.77 | 21.28 | 96.81 | 91.76 |
| 1 | 94.15 | 18.62 | 5.59 | 63.83 | 55.32 |
| 0.3 | 73.40 | −6.91 | −3.99 | 27.13 | 22.87 |
| 0.1 | 30.85 | −2.13 | −4.79 | 13.56 | 15.16 |

TABLE 8

Average Absorbance data for modified therapeutic agents with BSA.

| | With BSA | | | | |
|---|---|---|---|---|---|
| Conc/nM | APT070 | APT3098 | APT3328 | APT3330 | APT3331 |
| 300 | 0.086 | 0.051 | 0.060 | 0.041 | 0.059 |
| 100 | 0.054 | 0.062 | 0.046 | 0.057 | 0.062 |
| 30 | 0.078 | 0.048 | 0.086 | 0.074 | 0.063 |
| 10 | 0.097 | 0.084 | 0.157 | 0.106 | 0.143 |
| 3 | 0.119 | 0.105 | 0.168 | 0.167 | 0.168 |
| 1 | 0.175 | 0.172 | 0.195 | 0.191 | 0.201 |
| 0.3 | 0.210 | 0.187 | 0.203 | 0.224 | 0.203 |
| 0.1 | 0.203 | 0.226 | 0.211 | 0.224 | 0.218 |

$A_o = 0.057$
$A_{max} = 0.190$

TABLE 9

Average % Inhibition for modified therapeutic agents without BSA.

| | With BSA | | | | |
|---|---|---|---|---|---|
| Conc/nM | APT070 | APT3098 | APT3328 | APT3330 | APT3331 |
| 300 | 77.96 | 104.57 | 97.45 | 111.69 | 98.58 |
| 100 | 101.95 | 95.95 | 107.95 | 100.07 | 96.33 |
| 30 | 84.33 | 106.82 | 77.96 | 86.96 | 95.20 |
| 10 | 70.09 | 79.84 | 25.11 | 62.97 | 35.23 |
| 3 | 53.22 | 63.72 | 16.49 | 17.24 | 16.49 |
| 1 | 11.62 | 13.87 | −3.75 | −0.75 | −8.25 |
| 0.3 | −14.99 | 2.25 | −9.75 | −25.49 | −9.37 |
| 0.1 | −9.37 | −26.61 | −15.74 | −25.49 | −20.61 |

The data shows that the modified therapeutic agents retain activity following modification. The IH50 of a compound is the compound's concentration at which 50% inhibition of haemolysis of the erythrocytes is measured. This can be used is an indicator to the efficacy of the complement inhibitor.

The table below shows the IH50 of the tested compounds in the presence or absence of serum albumin.

TABLE 10

IH50 values for modified therapeutic agents

| | IH50 (nM) | |
|---|---|---|
| Compound | Absence of Albumin | Presence of Albumin (40 mg/ml) |
| APT070 control | 0.26 | 10.0 |
| APT3098 | 4.2 | 3.2 |
| APT3328 | 7.0 | 10.1 |
| APT3330 | 0.65 | 7.0 |
| APT3331 | 0.83 | 14.0 |

Hence in the presence of albumin the IH50 those agents with two lipophilic membrane binding elements according to the invention retained their activity to a greater extent that the APT070 control ie were less affected by the presence of albumin.

Example 2

Bis-Myristoylated CD59

CD59 is one of a number of complement system's regulators that prevents inappropriate activation. This regulator blocks the lytic activity of complement by binding to the C5b-8 and C5b-9 complexes and preventing formation of the polymeric C9 complex during the final stages of membrane attack complex (MAC) assembly on cell membranes. Human CD59 is a widely distributed glycoprotein which is anchored to the cell membrane via a glycophosphoinositol (GPI) moiety.

Expression of Recombinant Human CD59 (APT2439)

Recombinant human CD59 (lacking the GPI anchor), with an amino-terminal methionine and a carboxy-terminal cysteine (APT2439) was expressed in *E. coli*. The expression was codon optimised and under control of the T7 promoter, so that in the appropriate *E. coli* host strain, a λDE3 lysogen, the addition of the inducer iso-propyl β-D-thiogalactopyranoside (IPTG) to 1 mM resulted in expression of the target gene.

Refolding and Purification of APT2439

An *E. coli* cell pellet containing APT2439 as inclusion bodies was resuspended in a buffer containing 50 mM Tris, 1 mM EDTA, 0.1M NaCl adjusted to pH 8.0 with HCl, and lysed by two passages through an Emulsiflex C5 high pressure homogeniser (Glen Creston, UK) at 12000 psi. The inclusion bodies were isolated by centrifugation and purified by resuspension in a buffer containing 2% sodium deoxycholic acid and centrifugation as described above. This procedure was repeated several times. The purified inclusion bodies were solubilised in a buffer containing 8M urea, 5 mM dithiothreitol, 50 mM Tris, 1 mM EDTA, adjusted to pH 8.0 with HCl. Remaining insoluble material was removed by centrifugation. APT2439, contained in the supernatant, was refolded by diluting 50-fold into a buffer containing 50 mM Tris, 1 mM EDTA, 0.5M arginine, 3 mM cysteine, 1 mM cystine, adjusted to pH 8.0 with HCl, and incubation at 2-8° C. for 24 to 96 hours. The refolded protein was concentrated by ultrafiltration and extensively diafiltered against phosphate buffered saline at pH 7.3. Ammonium sulphate was added to a final concentration of 2.2M. Aggregated and misfolded protein was removed by centrifugation as describe above. The purified protein was diluted to reduce the concentration of ammonium sulphate and concentrated by ultrafiltration to about 100 μM.

Conjugation of APT2439 to APT2258 or APT3146.

The purified APT2439 was treated for 16 hours at room temperature with two molar equivalents of the reducing agent tris-2-carboxyethyl phosphine (TCEP), to generate a free thiol on the carboxy terminal cysteine of the protein. The protein was then incubated for two hours at room temperature with three molar equivalents of either APT2258 (Myr-GSSKSPSKKDDKKPGDC (2-SPy)-NH2; SEQ ID NO: 24) or APT3146 (thiopyridylated bisMyr-KSSKSPSKKD-DKKPGDC; SEQ ID NO: 25). The conjugation of APT2439 and APT2258 via a disulphide resulted in the formation of APT3073. The conjugation of APT2439 and APT3146 via a disulphide resulted in the formation of APT3280.

Purification of APT3073 and APT3280.

Ammonium sulphate was added to the conjugation mixtures described above (1.5M in the case of APT3073 and 1.0M in the case of APT3280) and the conjugates were purified by application to Toyopearl Phenyl 650M (Tosoh): The proteins were eluted in a linear decreasing gradient of ammonium sulphate.

Activity of APT2439, APT3073 and APT3280.

The ability of APT2439, APT3073 and APT3280 to inhibit MAC formation on guinea pig erythrocytes, was tested in a reactive lysis system. The effect of human albumin (HSA) on this activity was also investigated. Test samples were prepared at a range of concentrations in the presence or absence of 8 mg/ml fatty acid free HSA (Sigma, UK). 50 μL of these dilutions was added to 50 μL of a 5% suspension of guinea pig erythrocytes in PBS/0.1% gelatin, and incubated for 30 minutes at 37° C. 10 μL of human C5b6 complex (C5b6 was partially purified from acute phase serum) in PBS containing 15 mM EDTA and 0.1% gelatin, was added to the guinea pig erythrocyte suspension. 40 μL of normal human serum, diluted in PBS containing 15 mM EDTA and 0.1% gelatin was added as a source of C7, C8 and C9, and the suspension was incubated for 1 hour at 37 degrees Celsius. (The concentrations of C5b6 and normal human serum required to achieve about 80% lysis of guinea pig erythrocytes was pre-determined by titration.) The reaction mixtures were centrifuged for 5 minutes at 1000×g and the degree of haemolysis was determined by measuring the absorbance of the supernatant at 410 nm. To determine background lysis, a control reaction was prepared without serum. To determine maximal lysis, a control reaction containing no inhibitor (or test sample) was prepared. The percentage inhibition of haemolysis was determined for each protein at each concentration. An IH50 value (the concentration of protein required to achieve 50% inhibition of lysis) was determined for each protein in the presence and absence of HSA. IH50 values are presented in Table 11.

TABLE 11

IH50 values for modified therapeutic agent in the presence or absence of HSA.

| | IH50 (nM) | |
|---|---|---|
| Agent | Absence of HSA | Presence of HSA (2.7 mg/ml) |
| APT2439 | 600 | 400 |
| APT3073 | 0.8 | 6 |
| APT3280 | 0.1 | 0.08 |

In the absence of HSA, APT2439 was required at mM concentrations to achieve complete inhibition of haemolysis in the reactive lysis assay. APT3073 and APT3280 demonstrated about a 3-log and 4-log increase in potency respectively, compared to APT2439. In the presence of HSA (at a final concentration of 2.7 mg/ml) APT3073 demonstrated a 1-log decrease in potency compared to its potency in the absence of HSA. APT2439, APT3280 did not demonstrate any decrease in potency in the presence of HSA.

Example 3

Repeat of Bis-Myristoylated SCR1-3 Conjugation.

SCR1-3 (APT154) was modified with bismyristoyl as detailed above. APT154 was incubated overnight in 3-fold excess TCEP, then incubated for 2 hours with APT3146 (bis myristoyl) at a 10-fold excess. APT154 when derivatised with two myristoyl groups (APT 3147; bismyr-GSSKSPSKKKKKKPGDC conjugated to SCR1-3; SEQ ID NO: 26) was soluble under standard conditions. The activity of the conjugate was measured using the methods detailed above and summarised below.

Activity.

Multiple anti-haemolytic assays were performed on the reaction mixture of more than one batch of APT3147, in the presence and absence of fatty acid free bovine serum albumin (BSA) at both 4 mg/ml and 40 mg/ml, on non-stick plates.

The activity of both APT070 (single lipophilic membrane binding element) and APT3147 (two lipophilic membrane binding elements) was measured. The activity of APT3147 was less than APT070 in the absence of BSA, having IH50's of 0.26 and 2.2 respectively.

However, the activity of APT3147 was not affected by the presence of BSA even at a concentration of 40 mg/ml maintaining an IH50 of 2.2. By comparison, the activity of APT070 was reduced at a concentration of 4 and 40 mg/ml BSA to 1.3 and 10 respectively.

TABLE 12

Comparison of IH50 of a modified SCR1-3 with a single lipophilic element and two lipophilic elements.

| Compound | No BSA | 4 mg/ml BSA | 40 mg/ml BSA |
|---|---|---|---|
| APT070 | 0.26 | 1.3 | 10 |
| APT3147 | 2.2 | 2.2 | 2.2 |

Example 4

Vancomycin Conjugates

The lipophilic/basic tails were conjugated to Vancomycin by reaction with APT2033 (pyridyl dithioethyl Vancomycin carboxamide)

To each of nine tails APT2033 (3 equivalents) dissolved in water (1 mL) was added.

The nine reaction mixtures were stirred for 2 h at RT and the target compounds isolated by preparative HPLC. The majority of the solvent from each of the nine compounds was removed under reduced pressure to leave ~2 mL aqueous solution for each, which were lyophilised to yield fluffy white solids.

MIC Data

The activity of the modified Vancomycin was tested against two strains of bacteria.

MICS with *Bacillus subtilis* ATCC 6633 and *S. aureus* in NBS plate (μg/ml)

| Agent | B. substilis | S. aureus |
|---|---|---|
| APT3098 | >128 | >128 |
| APT3328 | 32 | >128 |
| APT3329 | 128 | >128 |
| APT3330 | 0.25 | 8 |// -continued
| Agent | B. substilis | S. aureus |
|---|---|---|
| APT3331 | 1 | 8 |
| APT3332 | <0.063 | <0.063 |
| APT3333 | 8 | >128 |
| APT3334 | 32 | >128 |
| APT3335 | 0.125 | 4 |

The results showed that the modified Vancomycin compounds retained activity the most effective being APT3332.

This application claims priority to GB0220936.9, filed Sep. 5, 2002, the entirety of which is hereby incorporated by reference.

---

The invention claimed is:

1. A modified therapeutic agent comprising:
   (a) a therapeutic agent which is a soluble protein, wherein the soluble protein is a complement inhibitor; and
   (b) three or more membrane binding elements with low membrane affinity covalently associated with the therapeutic agent;
   wherein the membrane binding elements comprise at least two lipophilic elements that comprise myristoyl groups, and
   a basic amino acid sequence selected from the group consisting of:

| GSSKSPSKKDDKKGDC, | [SEQ ID NO: 6] |
   | GSSKSPSKDKDKDGDC, | [SEQ ID NO: 7] |
   | KSSKSPSKKDDKKPGDC, | [SEQ ID NO: 8] |
   | KSSKSPSKDKDKDPGDC, | [SEQ ID NO: 9] |
   | and | |
   | KSKKKC, | [SEQ ID NO: 10] | wherein the membrane binding elements are capable of interacting independently and with thermodynamic additivity with components of cellular or artificial membranes exposed to extracellular fluids.

2. A modified therapeutic agent comprising:
   (a) a therapeutic agent which is a soluble protein, wherein the soluble protein is a complement inhibitor; and
   (b) three or more membrane binding elements with low membrane affinity covalently associated with the therapeutic agent;
   wherein the membrane binding elements comprise at least two lipophilic elements that comprise myristoyl groups, and
   a basic amino acid sequence selected from the group consisting of:

| KSSKSPSKKDDKKPGDC, | [SEQ ID NO: 8] |
   | KSSKSPSKDKDKDPGDC, | [SEQ ID NO: 9] |
   | and | |
   | KSKKKC; | [SEQ ID NO: 10] | wherein the membrane binding elements are capable of interacting independently and with thermodynamic additivity with components of cellular or artificial membranes exposed to extracellular fluids.

3. A modified therapeutic agent comprising:
(a) a therapeutic agent which is a soluble protein, wherein the soluble protein is a complement inhibitor; and
(b) three or more membrane binding elements with low membrane affinity covalently associated with the therapeutic agent;
wherein the membrane binding elements comprise at least two identical lipophilic elements that comprise myristoyl groups, and
a basic amino acid sequence selected from the group consisting of:

```
GSSKSPSKKDDKKGDC,       [SEQ ID NO: 6]
GSSKSPSKDKDKDGDC,       [SEQ ID NO: 7]
KSSKSPSKKDDKKPGDC,      [SEQ ID NO: 8]
KSSKSPSKDKDKDPGDC,      [SEQ ID NO: 9]
and
KSKKKC,                 [SEQ ID NO: 10]
``` wherein the membrane binding elements are capable of interacting independently and with thermodynamic additivity with components of cellular or artificial membranes exposed to extracellular fluids.

4. A pharmaceutical composition comprising a modified therapeutic agent according to claim 2 and a pharmaceutically acceptable excipient.

5. A modified therapeutic agent according to claim 2, wherein the agent is for use as a medicament.

6. An isolated intermediate for the preparation of a modified therapeutic agent, wherein the isolated intermediate comprises a conjugate consisting of:
(a) two lipophilic membrane binding elements, wherein the membrane binding elements comprise at least two lipophilic elements that are myristoyl groups; and
(b) a basic amino acid sequence selected from the group consisting of:

```
GSSKSPSKKDDKKGDC,       (SEQ ID NO: 6)
GSSKSPSKDKDKDGDC,       (SEQ ID NO: 7)
UKSSKSPSKKDDKKPGDC,     (SEQ ID NO: 8)
KSSKSPSKDKDKDPGDC,      (SEQ ID NO: 9)
and
KSKKKC                  (SEQ ID NO: 10).
```

7. A method of treatment of a disease or disorder amenable to treatment by a soluble therapeutic agent, which is a soluble protein, wherein the soluble protein is a complement inhibitor, which comprises administering a modified therapeutic agent according to claim 2.

8. A method of making a medicament for treatment of a disease or disorder, wherein the medicament is made by combining a modified therapeutic agent according to claim 2 and a pharmaceutically acceptable excipient.

9. A method for preparation of a modified therapeutic agent according to claim 2 whereby the membrane binding elements are added sequentially, with the first conjugated to the therapeutic agent, then subsequent elements are conjugated to each other.

10. A method for preparation of a modified therapeutic agent according to claim 1 whereby the membrane binding elements are prepared separately, the elements are conjugated to each other first, isolated, and then conjugated to the therapeutic agent.

11. A method for preparation of a modified therapeutic agent according to claim 2 whereby the membrane binding elements are prepared separately, the elements are conjugated to each other first, isolated, and then conjugated to the therapeutic agent.

12. A method for preparation of a modified therapeutic agent according to claim 3 whereby the membrane binding elements are prepared separately, the elements are conjugated to each other first, isolated, and then conjugated to the therapeutic agent.

13. A modified therapeutic agent according to claim 2, wherein the two myristoyl groups are in the form of a Bis-Myristoyl group attached at the N-terminal Lysine (K) of the basic amino acid sequence selected from the group consisting of SEQ ID NO: 8, SEQ ID NO: 9, and SEQ ID NO: 10.

14. A modified therapeutic agent according to claim 13, wherein the two myristoyl groups are in the form of a Bis-Myristoyl group attached to the basic amino acid sequence as N-alpha, N-Epsilon Bis-Myristoyl-L-Lysine.

15. A modified therapeutic agent according to claim 14, wherein the Bis-Myristoyl group and the basic amino acid sequence have a sequence selected from the group consisting of SEQ ID NO: 15, SEQ ID NO: 16, and SEQ ID NO: 17.

16. A modified therapeutic agent according to claim 15, wherein the Bis-Myristoyl group and the basic amino acid sequence have the sequence SEQ ID NO: 15.

17. An isolated intermediate for the preparation of a modified therapeutic agent according to claim 13 comprising a conjugate consisting of a Bis-Myristoyl group attached at the N-terminal Lysine (K) of the basic amino acid sequence selected from the group consisting of SEQ ID NO: 8, SEQ ID NO: 9, and SEQ ID NO: 10.

18. An isolated intermediate for the preparation of a modified therapeutic agent according to claim 14 comprising a conjugate consisting of a Bis-Myristoyl group attached as N-alpha, N-Epsilon Bis-Myristoyl-L-Lysine at the N-terminal Lysine (K) of the basic amino acid sequence selected from the group consisting of SEQ ID NO: 8, SEQ ID NO: 9, and SEQ ID NO: 10.

19. A method for preparation of a modified therapeutic agent according to claim 13, whereby the membrane binding elements are prepared separately, the elements are conjugated to each other first, isolated, and then conjugated to the therapeutic agent.

20. A method for preparation of a modified therapeutic agent according to claim 14, whereby the membrane binding elements are prepared separately, the elements are conjugated to each other first, isolated, and then conjugated to the therapeutic agent.

21. A method for preparation of a modified therapeutic agent according to claim 15, whereby the membrane binding elements are prepared separately, the elements are conjugated to each other first, isolated, and then conjugated to the therapeutic agent.

22. A method for preparation of a modified therapeutic agent according to claim 16, whereby the membrane binding elements are prepared separately, the elements are conjugated to each other first, isolated, and then conjugated to the therapeutic agent.

23. A pharmaceutical composition comprising a modified therapeutic agent according to claim 1 and a pharmaceutically acceptable excipient.

24. A modified therapeutic agent according to claim 1, wherein the agent is for use as a medicament.

25. A pharmaceutical composition comprising a modified therapeutic agent according to claim 3 and a pharmaceutically acceptable excipient.

26. A modified therapeutic agent according to claim 3, wherein the agent is for use as a medicament.

27. An isolated intermediate for the preparation of a modified therapeutic agent according to claim 14 comprising a conjugate consisting of a Bis-Myristoyl group attached as N-alpha, N-Epsilon Bis-Myristoyl-L-Lysine at the N-terminal Lysine (K) of the basic amino acid sequence selected from the group consisting of SEQ ID NO: 8, SEQ ID NO: 9, and SEQ ID NO: 10.

28. A modified therapeutic agent comprising:
(a) a therapeutic agent which is a soluble protein, wherein the soluble protein is a complement inhibitor; and
(b) three or more membrane binding elements with low membrane affinity covalently associated with the therapeutic agent;

wherein the membrane binding elements comprise at least two identical lipophilic elements that comprise myristoyl groups, and a basic amino acid sequence selected from the group consisting of:

| | |
|---|---|
| KSSKSPSKKDDKKPGDC, | [SEQ ID NO: 8] |
| KSSKSPSKDKDKDPGDC, and | [SEQ ID NO: 9] |
| KSKKKC, | [SEQ ID NO: 10] | wherein the membrane binding elements are capable of interacting independently and with thermodynamic additivity with components of cellular or artificial membranes exposed to extracellular fluids.

* * * * *

UNITED STATES PATENT AND TRADEMARK OFFICE
CERTIFICATE OF CORRECTION

PATENT NO. : 8,455,447 B2  
APPLICATION NO. : 12/688252  
DATED : June 4, 2013  
INVENTOR(S) : Dirk Esser et al.

Page 1 of 1

It is certified that error appears in the above-identified patent and that said Letters Patent is hereby corrected as shown below:

Title Page, Column 1, Item (63) delete the information under "Related U.S. Application Data" and insert the following:

--Continuation of application No. 10/526,808 filed June 8, 2005, now abandoned, which is a 371 of PCT/GB03/03867 filed September 5, 2003.--

Signed and Sealed this  
Thirty-first Day of December, 2013

Margaret A. Focarino  
*Commissioner for Patents of the United States Patent and Trademark Office*

SEQUENCE LISTING

```
<160> NUMBER OF SEQ ID NOS: 26

<210> SEQ ID NO 1
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 1

Asp Gly Pro Lys Lys Lys Lys Lys Ser Pro Ser Lys Ser Gly
1               5                   10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 2

Gly Ser Ser Lys Ser Pro Ser Lys Lys Lys Lys Lys Pro Gly Asp
1               5                   10                  15

Cys

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 3

Ser Pro Ser Asn Glu Thr Pro Lys Lys Lys Lys Lys Arg Phe Ser Phe
1               5                   10                  15

Lys Lys Ser Gly
            20

<210> SEQ ID NO 4
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 4

Cys Asp Gly Pro Lys Lys Lys Lys Lys Lys Ser Pro Ser Lys Ser Ser
1               5                   10                  15
```

Lys

<210> SEQ ID NO 5
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 5

Ser Lys Asp Gly Lys Lys Lys Lys Lys Ser Lys Thr Lys Cys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 6

Gly Ser Ser Lys Ser Pro Ser Lys Lys Asp Asp Lys Lys Gly Asp Cys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 7

Gly Ser Ser Lys Ser Pro Ser Lys Asp Lys Asp Lys Asp Gly Asp Cys
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 8

Lys Ser Ser Lys Ser Pro Ser Lys Lys Asp Asp Lys Lys Pro Gly Asp
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 9

Lys Ser Ser Lys Ser Pro Ser Lys Asp Lys Asp Lys Asp Pro Gly Asp
1               5                   10                  15

Cys

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Lys Ser Lys Lys Lys Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Gly Arg Gly Asp Ser Pro
1               5

<210> SEQ ID NO 12
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 12

Asp Gly Pro Ser Glu Ile Leu Arg Gly Asp Phe Ser Ser Cys
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 13

Gly Asn Glu Gln Ser Phe Arg Val Asp Leu Arg Thr Leu Leu Arg Tyr
1               5                   10                  15

Ala

<210> SEQ ID NO 14
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 14

Gly Phe Arg Ile Leu Leu Lys Val
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-MYRISTOYL-

<400> SEQUENCE: 15

Lys Ser Ser Lys Ser Pro Ser Lys Lys Asp Asp Lys Lys Pro Gly Asp
1               5                   10                  15

Cys

<210> SEQ ID NO 16

```
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-MYRISTOYL-

<400> SEQUENCE: 16

Lys Ser Ser Lys Ser Pro Ser Lys Asp Lys Asp Lys Asp Pro Gly Asp
1               5                   10                  15

Cys

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-MYRISTOYL-

<400> SEQUENCE: 17

Lys Ser Lys Lys Lys Cys
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-DECANOYL-

<400> SEQUENCE: 18

Lys Ser Ser Lys Ser Pro Ser Lys Lys Asp Asp Lys Lys Pro Gly Asp
1               5                   10                  15

Cys

<210> SEQ ID NO 19
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-DECANOYL-

<400> SEQUENCE: 19

Lys Ser Ser Lys Ser Pro Ser Lys Asp Lys Asp Lys Asp Pro Gly Asp
1               5                   10                  15

Cys

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: BIS-DECANOYL-

<400> SEQUENCE: 20

Lys Ser Lys Lys Lys Cys
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-HEXANOYL-

<400> SEQUENCE: 21

Lys Ser Ser Lys Ser Pro Ser Lys Lys Asp Asp Lys Lys Pro Gly Asp
1               5                   10                  15

Cys

<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-HEXANOYL-

<400> SEQUENCE: 22

Lys Ser Ser Lys Ser Pro Ser Lys Asp Lys Asp Lys Asp Pro Gly Asp
1               5                   10                  15

Cys

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: BIS-HEXANOYL-

<400> SEQUENCE: 23

Lys Ser Lys Lys Lys Cys
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: MYRISTOL-
<220> FEATURE:
<221> NAME/KEY: MISC_FEATURE
<222> LOCATION: (18)..(18)
<223> OTHER INFORMATION: (2-SPY)-NH2
```

```
<400> SEQUENCE: 24

Gly Ser Ser Lys Ser Pro Ser Lys Lys Asp Asp Lys Lys Pro Gly Asp
1               5                   10                  15

Cys

<210> SEQ ID NO 25
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: THIOPYRIDYLATED BIS-MYRISTOL-

<400> SEQUENCE: 25

Lys Ser Ser Lys Ser Pro Ser Lys Lys Asp Asp Lys Lys Pro Gly Asp
1               5                   10                  15

Cys

<210> SEQ ID NO 26
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (18)..(18)
<223> OTHER INFORMATION: conjugated to SCR-1-3
<220> FEATURE:
<221> NAME/KEY: MISC_FEATURE
<222> LOCATION: (1)..(1)
<223> OTHER INFORMATION: BIS-MYRISTOL-

<400> SEQUENCE: 26

Gly Ser Ser Lys Ser Pro Ser Lys Lys Lys Lys Lys Lys Pro Gly Asp
1               5                   10                  15

Cys
```